(12) United States Patent
Richey

(10) Patent No.: US 11,154,327 B2
(45) Date of Patent: Oct. 26, 2021

(54) VAGINAL SURGICAL APPARATUS

(71) Applicant: Mark Edmund Richey, Anchorage, AK (US)

(72) Inventor: Mark Edmund Richey, Anchorage, AK (US)

(73) Assignee: FRESHWATER BAY INDUSTRIES, LLC, Anchorage, AK (US)

(*) Notice: Subject to any disclaimer, the term of this patent is extended or adjusted under 35 U.S.C. 154(b) by 242 days.

(21) Appl. No.: 16/427,206

(22) Filed: May 30, 2019

(65) Prior Publication Data

US 2019/0321080 A1    Oct. 24, 2019

Related U.S. Application Data

(63) Continuation-in-part of application No. 16/030,701, filed on Jul. 9, 2018, now Pat. No. 10,327,813, which (Continued)

(51) Int. Cl.
*A61B 17/42* (2006.01)
*A61B 1/00* (2006.01)
(Continued)

(52) U.S. Cl.
CPC ...... *A61B 17/4241* (2013.01); *A61B 1/00066* (2013.01); *A61B 1/00179* (2013.01);
(Continued)

(58) Field of Classification Search
CPC . A61B 17/4241; A61B 17/0483; A61B 1/303; A61B 1/0684; A61B 1/00066;
(Continued)

(56) References Cited

U.S. PATENT DOCUMENTS 1,940,122 A   8/1931   Gardner
3,587,588 A   9/1968   Murr
(Continued)

FOREIGN PATENT DOCUMENTS

RU   81947    10/2003
RU   44050    2/2005
SU   133553   10/1960

OTHER PUBLICATIONS

Nygaard et al. "Abdominal Sacrosolpolexy: A Comprehensive Review", Obstet Gyne, Oct. 2004, 104(4)805-823.
(Continued)

*Primary Examiner* — Christine H Matthews
*Assistant Examiner* — Joshua Daryl D Lannu
(74) *Attorney, Agent, or Firm* — Ruttler Mills PLLC; James J. Ruttler

(57) ABSTRACT

This invention relates generally to a medical device, and more specifically, to a vaginal surgical apparatus. In one embodiment, an apparatus includes, a vaginal manipulator probe that is at least partly insertable into a vagina, the vaginal manipulator probe including an end portion that includes a bullous tip and that includes a space that accommodates a cervix therewithin; and at least one prominence incorporated with the vaginal manipulator probe operable to assist with identifying one or more positions of at least one anatomical structure or orienting the vaginal manipulator probe.

22 Claims, 11 Drawing Sheets

Related U.S. Application Data is a continuation of application No. PCT/US2016/037014, filed on Jun. 10, 2016, and a continuation of application No. 15/691,194, filed on Aug. 30, 2017, now Pat. No. 10,052,131, which is a continuation of application No. 15/480,227, filed on Apr. 5, 2017, now Pat. No. 10,052,130, which is a continuation of application No. 15/208,867, filed on Jul. 13, 2016, now Pat. No. 9,655,646, which is a continuation of application No. 15/179,215, filed on Jun. 10, 2016, and a continuation-in-part of application No. 13/852,784, filed on May 31, 2013, now Pat. No. 10,166,044, and a continuation-in-part of application No. 14/971,512, filed on Dec. 16, 2015, now abandoned.

(60) Provisional application No. 62/174,127, filed on Jun. 11, 2015, provisional application No. 62/193,721, filed on Jul. 17, 2015, provisional application No. 62/252,810, filed on Nov. 9, 2015, provisional application No. 62/257,090, filed on Nov. 18, 2015, provisional application No. 62/265,038, filed on Dec. 9, 2015, provisional application No. 62/312,069, filed on Mar. 23, 2016.

(51) Int. Cl.

| | | |
|---|---|---|
| *A61B 90/00* | (2016.01) | |
| *A61B 1/303* | (2006.01) | |
| *A61M 37/00* | (2006.01) | |
| *A61B 17/04* | (2006.01) | |
| *A61B 1/06* | (2006.01) | |
| *A61M 31/00* | (2006.01) | |
| *A61B 17/00* | (2006.01) | |
| *A61B 90/30* | (2016.01) | |

(52) U.S. Cl.
CPC .......... *A61B 1/0623* (2013.01); *A61B 1/0684* (2013.01); *A61B 1/303* (2013.01); *A61B 17/0483* (2013.01); *A61B 17/42* (2013.01); *A61B 90/03* (2016.02); *A61B 90/36* (2016.02); *A61B 90/361* (2016.02); *A61B 90/37* (2016.02); *A61M 37/00* (2013.01); *H05K 999/99* (2013.01); *A61B 2017/00022* (2013.01); *A61B 2017/0046* (2013.01); *A61B 2017/00084* (2013.01); *A61B 2017/00115* (2013.01); *A61B 2017/00424* (2013.01); *A61B 2017/00473* (2013.01); *A61B 2017/4225* (2013.01); *A61B 2090/036* (2016.02); *A61B 2090/08021* (2016.02); *A61B 2090/309* (2016.02); *A61B 2090/3945* (2016.02); *A61M 31/00* (2013.01)

(58) Field of Classification Search
CPC ...... A61B 1/00179; A61B 2017/00473; A61B 90/36; A61B 2090/036; A61B 90/03; A61B 2017/00424; A61B 90/37; A61B 90/361; A61B 1/0623
See application file for complete search history.

(56) References Cited

U.S. PATENT DOCUMENTS

| | | | |
|---|---|---|---|
| 4,198,982 | A | 4/1980 | Fortner |
| 4,710,075 | A | 12/1987 | Davison |
| 4,877,037 | A * | 10/1989 | Ko .......... A61B 17/34 |
| | | | 600/569 |
| 5,409,496 | A | 4/1995 | Rowden |
| 5,421,346 | A | 6/1995 | Sanyal |
| 5,792,053 | A | 8/1998 | Skladnev et al. |
| 8,292,901 | B2 | 10/2012 | Auerbach et al. |
| 8,460,209 | B2 | 6/2013 | Klein |
| 8,976,363 | B2 | 3/2015 | Bendall et al. |
| 2003/0187334 | A1 | 10/2003 | Biswas |
| 2005/0137557 | A1 | 6/2005 | Swiecicki et al. |
| 2008/0221590 | A1 | 9/2008 | Ikeda et al. |
| 2009/0204126 | A1 | 8/2009 | Le |
| 2010/0106163 | A1 | 4/2010 | Blair et al. |
| 2010/0168784 | A1 | 7/2010 | Pustilnik |
| 2010/0274087 | A1 | 10/2010 | Diolaiti et al. |
| 2012/0016185 | A1 | 1/2012 | Sherts |
| 2012/0203244 | A1* | 8/2012 | McDonald ....... A61B 17/12099 |
| | | | 606/119 |
| 2012/0289858 | A1 | 11/2012 | Ouyang |
| 2012/0330324 | A1 | 12/2012 | Sauer |
| 2013/0072749 | A1* | 3/2013 | Fairneny ................ A61B 90/30 |
| | | | 600/37 |
| 2013/0197537 | A1 | 8/2013 | Fairneny |
| 2015/0005780 | A1 | 1/2015 | Einarsson |

OTHER PUBLICATIONS

Richard M. Lebovitz, Jeffrey N. Fredman, and Jeffrey B. Robertson, Ex parte Mark Edmund Richey Decision on Appeal, Jun. 19, 2018. Appeal 2017-006891, U.S. Appl. No. 13/852,784, Technology Center 3700.

* cited by examiner

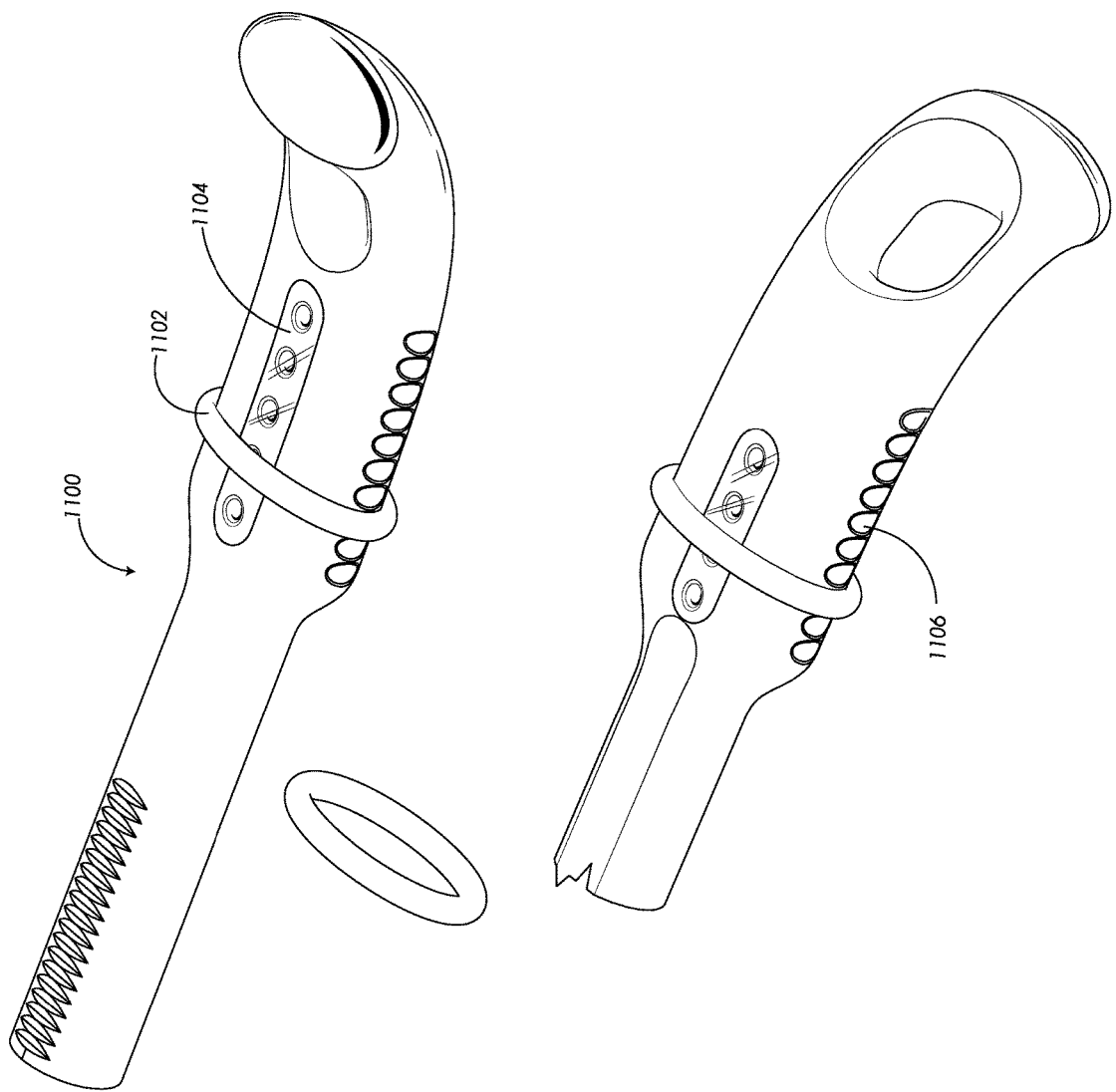

VAGINAL SURGICAL APPARATUS

PRIORITY CLAIM

This application is a continuation-in-part of U.S. non-provisional patent application Ser. No. 16/030,701 filed on Jul. 9, 2018, which is a continuation of International Application PCT/US16/37014 filed on Jun. 10, 2016, and U.S. non-provisional patent application Ser. No. 15/691,194 filed Aug. 30, 2017, which is a continuation of U.S. non-provisional patent application Ser. No. 15/480,227 filed on Apr. 5, 2017, which is a continuation of Ser. No. 15/208,867 filed Jul. 13, 2016, which is a continuation of Ser. No. 15/179,215 filed Jun. 10, 2016, which application is (a) a non-provisional patent application of U.S. provisional patent application 62/174,127 filed Jun. 11, 2015; U.S. provisional patent application 62/193,721 filed Jul. 17, 2015; U.S. provisional patent application 62/252,810 filed Nov. 9, 2015; U.S. provisional patent application 62/257,090 filed Nov. 18, 2015; U.S. provisional patent application 62/265,038 filed Dec. 9, 2015; and U.S. provisional patent application 62/312,069 filed Mar. 23, 2016; (b) a continuation-in-part of U.S. non-provisional patent application Ser. No. 13/852,784 filed May 31, 2013; and (c) a continuation-in-part of U.S. nonprovisional patent application Ser. No. 14/971,512 filed Dec. 16, 2015.

This application claims the benefit of and/or priority to each of the foregoing patent applications and any and all parent, grandparent, and great-grandparent applications thereof. The foregoing patent applications are incorporated by reference in their entirety as if fully set forth herein.

FIELD OF THE INVENTION

This invention relates generally to a medical device, and more specifically, to a vaginal surgical apparatus.

SUMMARY

This invention relates generally to a medical device, and more specifically, to a vaginal surgical apparatus. In one embodiment, an apparatus includes, but is not limited to, an elongated handle portion; a vaginal manipulator probe that is at least partly insertable into a vagina, the vaginal manipulator probe extending from the elongated handle portion and including an arcuate end portion, the arcuate end portion including an aperture for accommodating a cervix; and a disk that is movable along at least a portion of a length of the vaginal manipulator probe, the disk including a locking mechanism to releasably secure the disk in position to limit vaginal insertion depth of the vaginal manipulator probe. In another embodiment, an apparatus includes, but is not limited to, an elongated handle portion that includes a first bollard tab and a second bollard tab for releasably securing a suture; a vaginal manipulator probe extending from the elongated handle portion and including an arcuate end portion having an oval-cross sectional shape and having an aperture channel for accommodating a cervix; and a disk that is movable along at least a portion of a length of the vaginal manipulator probe, the disk including a locking mechanism to releasably secure the disk in position to limit vaginal insertion depth of the vaginal manipulator probe. In a further embodiment, an apparatus includes, but is not limited to, an elongated handle portion that includes a first bollard tab and a second bollard tab for releasably securing a suture; a vaginal manipulator probe extending from the elongated handle portion and including an arcuate end portion having an oval-cross sectional shape and having an aperture channel for accommodating a cervix, the arcuate end portion terminating to a bullous tip; a disk including a sleeve and shoulder, the disk being movable along at least a portion of a length of the vaginal manipulator probe; and a spring loaded latch associated with the disk to releasably secure the disk in position along a length of the vaginal manipulator probe to limit vaginal insertion depth. In yet an additional embodiment, an apparatus includes, but is not limited to, a handle portion; a vaginal manipulator probe that is at least partly insertable into a vagina, the vaginal manipulator probe extending from the handle portion and including an arcuate end portion, the arcuate end portion including an channel for accommodating a cervix; one or more LED lights disposed on the vaginal manipulator probe for illuminating vaginal tissue; at least one camera positioned with a field of view of the channel to permit visualization of a cervix relative to the channel; at least one battery receptacle within the handle portion; at least one button or switch operable to control operation of the one or more LED lights; at least one communication link for transferring image data to at least one display unit, the at least one communication link being either a wired communication link or a wireless communication link; and a disk that is movable along at least a portion of a length of the vaginal manipulator probe, the disk including a locking mechanism to releasably secure the disk in position along the portion of the length of the vaginal manipulator probe to limit vaginal insertion depth of the vaginal manipulator probe.

BRIEF DESCRIPTION OF THE DRAWINGS

Embodiments of the present invention are described in detail below with reference to the following drawings.

FIG. 11 is a perspective view of a vaginal surgical apparatus with one or more movable prominence features, in accordance with an embodiment of the invention.

DETAILED DESCRIPTION

This invention relates generally to a medical device, and more specifically, to a vaginal surgical apparatus. Certain embodiments of the invention are set forth in the following description and in FIGS. 1-11 to provide a thorough understanding of such embodiments. The present invention may have additional embodiments, may be practiced without one or more of the details described for any particular described embodiment, or may have any detail described for one particular embodiment practiced with any other detail described for another embodiment.

Figure 1:
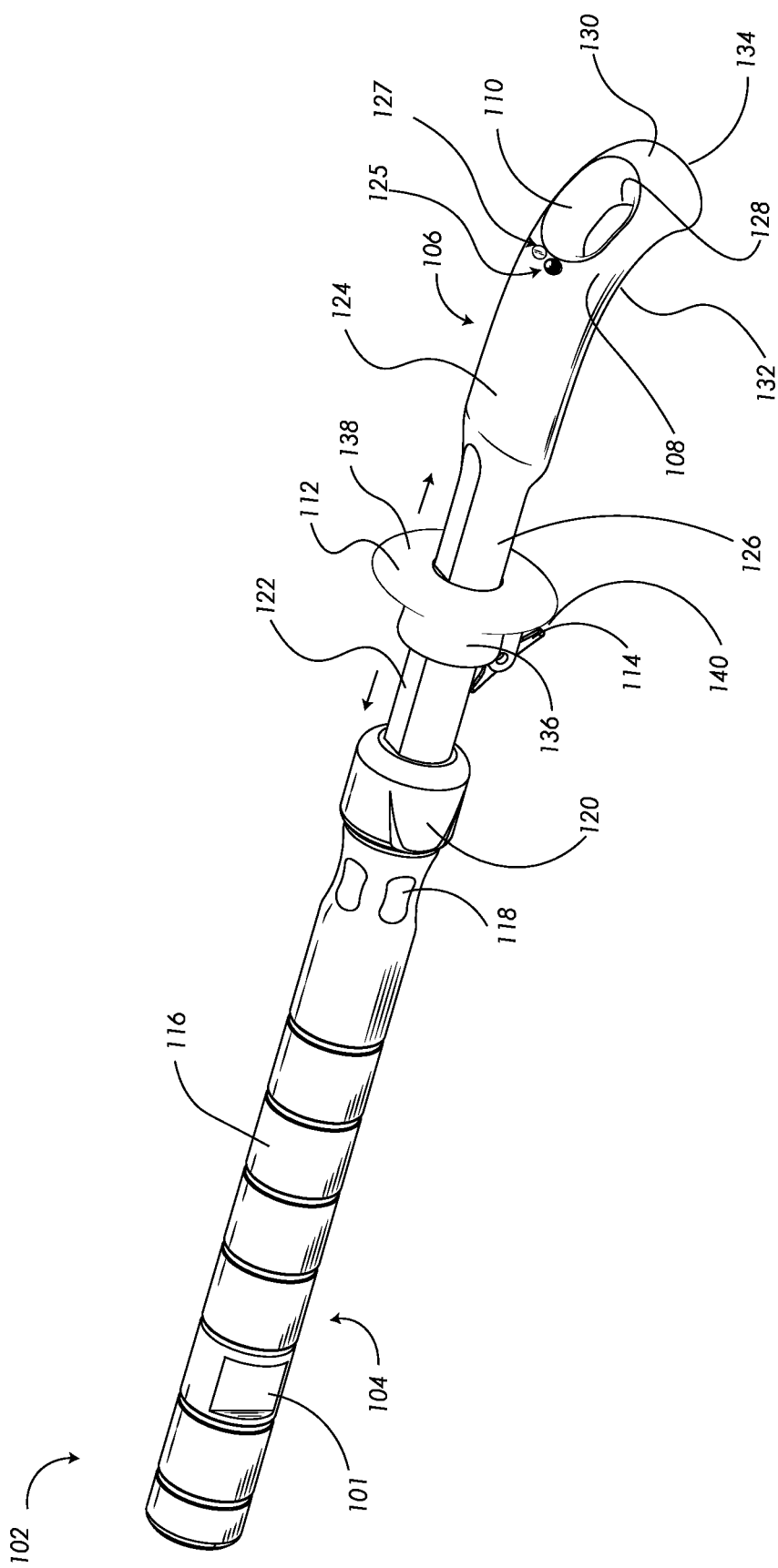
FIG. 1 is a top perspective view of a vaginal surgical apparatus, in accordance with an embodiment of the invention.

FIG. 1 is a top perspective view of a vaginal surgical apparatus, in accordance with an embodiment of the invention. In one embodiment, an apparatus 102 includes, but is not limited to, an elongated handle portion 104; a vaginal manipulator probe 106 that is at least partly insertable into a vagina, the vaginal manipulator probe 106 extending from the elongated handle portion 104 and including an arcuate end portion 108, the arcuate end portion 108 including an aperture 110 for accommodating a cervix; and a disk 112 that is movable along at least a portion of a length of the vaginal manipulator probe 106, the disk 112 including a locking mechanism 114 to releasably secure the disk 112 in position to limit vaginal insertion depth of the vaginal manipulator probe 106. In one particular embodiment, the elongated handle portion 104 is a cylindrical shaft 116. In another embodiment, the elongated handle portion 104 includes a recessed waist portion 118. In certain embodiments, the vaginal manipulator probe 106 is releasable from the elongated handle portion 104. Alternatively, in some embodiments, the vaginal manipulator probe 106 and the elongated handle portion 104 are a unitary structure. In one embodiment, the elongated handle portion 104 includes a first bollard tab 120 and a second bollard tab (not visible) opposite the first bollard tab 120 for releasably securing a suture. In further embodiments, the vaginal manipulator probe 106 has an oval cross-sectional shape along a length of a longitudinal axis of the vaginal manipulator probe 106. In one particular embodiment, the vaginal manipulator probe 106 includes a first portion 122 having a first cross-sectional width that flares to a second portion 124 having a second cross-sectional width that is greater than the first-cross-sectional width, wherein the first portion 122 and the second portion 124 have substantially similar cross-sectional heights. In some embodiments, the vaginal manipulator probe 106 includes a notch track (not visible) for interfacing with the locking mechanism 114 of the disk 112. In additional embodiments, the vaginal manipulator probe 106 includes a linear portion 126 that extends from the arcuate end portion 108. In one particular embodiment, the aperture 110 of the arcuate end portion 108 of the vaginal manipulator probe 106 extends as a channel 128 from a top surface 130 of the vaginal manipulator probe 106 through to a bottom surface 132 of the vaginal manipulator probe 106. In one embodiment, the aperture 110 is positioned approximately midway along a length of the arcuate end portion 108 of the vaginal manipulator probe 106. In other embodiments, the vaginal manipulator probe 106 includes an end portion 134 that curls to define a bullous tip (not visible). In one specific embodiment, the aperture 110 measures approximately 2 cm to 4 cm across and/or in length. In some embodiments, the disk 112 is movable along a portion of a length of the vaginal manipulator probe 106 having a notch track (not visible). In further embodiments, the disk 112 includes a sleeve portion 136 that circumscribes the vaginal manipulator probe 106. In other embodiments, the disk 112 includes a shoulder 138 that circumscribes the vaginal manipulator probe 106, the shoulder 138 being operable to rest against an outside surface of a vulva when the vaginal manipulator probe 106 is inserted within the vagina. In a further embodiment, the disk 112 includes a spring-loaded latch 140 that is tensionally biased against a notch track (not visible) of the vaginal manipulator probe 106.

In one embodiment, an apparatus 102 includes, but is not limited to, an elongated handle portion 104 that includes a first bollard tab 120 and a second bollard tab (not visible) for releasably securing a suture; a vaginal manipulator probe 106 extending from the elongated handle portion 104 and including an arcuate end portion 108 having an oval-cross sectional shape and having an aperture channel 110 for accommodating a cervix; and a disk 112 that is movable along at least a portion of a length of the vaginal manipulator probe 106, the disk 112 including a locking mechanism 114 to releasably secure the disk 112 in position to limit vaginal insertion depth of the vaginal manipulator probe 106.

In another embodiment, an apparatus 102 includes, but is not limited to, an elongated handle portion 104 that includes a first bollard tab 120 and a second bollard tab (not visible) for releasably securing a suture; a vaginal manipulator probe 106 extending from the elongated handle portion 104 and including an arcuate end portion 108 having an oval-cross sectional shape and having an aperture channel 110 for accommodating a cervix, the arcuate end portion 108 terminating to a bullous tip (not visible); a disk 112 including a sleeve 136 and shoulder 138, the disk 112 being movable along at least a portion of a length of the vaginal manipulator probe 106; and a spring loaded latch 140 associated with the disk 112 to releasably secure the disk 112 in position along a length of the vaginal manipulator probe 106 to limit vaginal insertion depth.

In one embodiment, the elongated handle portion 104 includes a notch 101 on opposing sides to define a surface for securing the apparatus 102, such as using a locking mechanism, clamp, clasp associated with a table or resting surface.

In some embodiments, the cylindrical shaft 116 is non-cylindrical such as oval, square, triangular, or irregular in shape. In other embodiments, the cylindrical shaft 116 is non-linear, such as including a bend or curve along its length. In further embodiments, the notch 101 is omitted or substituted with a hole, channel, or protrusion. Alternatively, a clamp, clasp, or other securing mechanism can be included with the cylindrical shaft 116 to facilitate securing the apparatus 102 to a table, support, stand, or other structure. In some embodiments, the recessed waist 118 is omitted or can be duplicated at different positions along a length of the cylindrical shaft to provide additional grip points. In certain embodiments, the first bollard tab 120 and the second bollard tab 202 can be omitted or positionable on a rotatably lockable or slidable sleeve that permits different alignment/positioning. In an additional embodiment, the cylindrical shaft 116 can be tapped with threads to permit screwing and unscrewing of the vaginal manipulator probe 106. Alternatively, the cylindrical shaft 116 can include a tapered, friction, bearing, post, groove, or other locking mechanism for removably securing the vaginal manipulator probe 106.

In an additional embodiment, the vaginal manipulator probe 106 is arcuate along a substantially entire length (e.g., curved along a majority of the length without having the linear portion 126). The arcuate end portion 108 can have a curvature as depicted or alternatively can be curved to a greater or lesser extent as desired to accommodate the vaginal anatomy. In certain embodiments, the arcuate end portion 108 can include an adjustable curvature to permit point-of-use adjustment by a health provider or doctor. Alternatively, the vaginal manipulator probe 106 can be substantially linear along its substantially entire length (e.g., not including the arcuate end portion 108). In certain embodiments, the linear portion 126 and the arcuate end portion 108 have a circular, oval, square, triangular, irregular, or other similar cross-sectional shape, which may be the same or different between the two. In another embodiment, the linear portion 126 and the arcuate end portion 108 have substantially similar widths or heights or can have differing widths or heights. In other embodiments, the arcuate end portion 108 can include a larger or smaller flare from the linear portion 126 to define a wider or narrower shape. In some embodiments, the arcuate end portion 108 can have a varying diameter, height, or cross sectional shape along its length. In other embodiments, the end portion 134 is flat, curved, pointed, conical, or has another similar shape. In a further embodiment, the aperture 110 can be a surface indentation or can extend fully or partly through the vaginal manipulator probe 106. In one particular embodiment, walls of the aperture 110 are tapered in or out to define a surface for accommodating various anatomical features. The aperture 110 can be square, rectangular, oval, circular, triangular, or another similar shape. The aperture 110 can be positioned further towards the end portion 134 or further towards the linear portion 126. The aperture 110 can extend further along a length of the arcuate end portion 108 or can be shortened. Additionally, in some embodiments, the aperture 110 can be adjustable in width, height, depth, diameter, or shape. In other embodiments, the disk 112 can include a larger or a smaller diameter shoulder 138. The sleeve portion 136 can be omitted or extended further forward or aft to cover more of the linear portion 126. The linear portion 126 can include measurement markings to indicate a distance of insertion from the end portion 134. The locking mechanism 114 can be omitted or substituted, such as with a threaded disk that rotates, a pin and hole, a screw and track, or another similar structure.

In additional embodiments, the apparatus 102 includes one or more cameras 127 positioned at one or more points to provide visual feedback, such as proximate the end portion 134, along a length of the arcuate end portion 108, or proximate the aperture 110, as depicted. In certain embodiments, the one or more cameras 127 can be disposed on a top surface 130 of the vaginal manipulator probe 106 or on a bottom surface 132 of the vaginal manipulator probe or even on either side of the vaginal manipulator probe 106. In one particular embodiment, the one or more cameras 127 are disposed on a top surface 130 and are angled to permit visualization of the aperture 110 relative to the cervix to facilitate proper positioning of the cervix within the aperture 110. Alternatively, the one or more cameras 127 can be positioned along the vaginal manipulator probe 106—either on the linear portion 126 or the arcuate end portion 108—permitting visualization of the vaginal manipulator probe 106 relative to various vaginal anatomical structures and/or one or more needles or surgical tools. In certain embodiments, the one or more LED lights 125 are positioned to illuminate the aperture 110 to facilitate imaging using the one or more cameras 127. The one or more LED lights 125 are depicted as being proximate the one or more cameras 127 and positioned to illuminate the aperture 110. However, the one or more LED lights 125 are not limited to being positioned as depicted. For example, in certain embodiments, the apparatus 102 includes one or more LED lights 125 surrounding the aperture 110, which one or more LED lights 125 emit light that is detectable through the tissue of a cervix and trans-illuminate tissue of the vagina. This positioning of the one or more LED lights 125 facilitates correct positioning of the vaginal manipulator probe 106 relative to the cervix. The one or more LED lights 125 can be disposed around the aperture 110 on the inside diameter walls or near a lip on the top surface 130 or the bottom surface 132. The one or more LED lights 125 can be positioned anywhere on the arcuate end portion 108 or the linear portion 126. Alternatively, the one or more LED lights 125 can be disposed anywhere along the vaginal manipulator probe 106 or even along the elongated handle portion 104. Thus, in certain embodiments, the one or more cameras 127 at a vantage point to visualize the aperture 110, with the one or more LED lights 125 adjacent. Another location for the one or more LED lights 125 is on the top of a cervical "ring" in a series all around the aperture 110, which would be in direct contact with the vagina where the vagina attaches to the cervix, thereby trans-illuminating the vagina at that junction for the surgeon/health provider to see from an abdominal perspective. Alternatively, the one or more LED lights 125 could be in a small series of 3 or 4 lights at the junction of the vaginal manipulator probe 106 where it transitions to the aperture 110. Additionally, the vaginal manipulator probe 106 is configured to change or emit color/light, such as using one or more internal or externally mounted LED lights 125 to provide contrast relative to tissue or blood. Batteries in any of these embodiments can be disposed within the elongated handle portion 104.

In one particular embodiment, a display screen is included to permit display of one or more images/video captured using the one or more cameras 127. The display screen can be integrated or coupled to the elongated handle portion 104 or can be detachable and removably couplable to the elongated handle portion. The display screen can be pivoted, angled, shifted, moved to permit visualization by a healthcare provider during application. The display screen can be disposable or reusable. The display screen can include or be associated with one or more buttons or switches to permit control of the one or more LED lights 125 or the one or more cameras 127. For instance, the one or more LED lights 125 can be turned on or off or have varying intensity or color. Additionally, the one or more cameras 127 can be robotically moved, angled, shifted or can even enable zoom, image, video, contrast, etc. changes.

In further embodiments, the arcuate end portion 108 includes one or more indentations or grooves on its surface to backstop a needle, similar in function to a thimble. In some embodiments, one or more physiological sensors are disposed on a surface of the apparatus 102 or internally of the apparatus 102, such physiological sensors can provide data feedback regarding temperature, chemical, coloration, or other similar information. In certain embodiments, the apparatus 102 includes an internal conduit that exits via the end portion 134 or via one or more pores in the vaginal manipulator probe 106 for medication or fluid delivery. The internal conduit can include an attachment point in the elongated handle portion for coupling with a catheter or other conduit for receiving fluids or medication. Alternatively, the internal conduct can extend from a refillable reservoir disposed within the apparatus 102 for containing fluid or medication. The apparatus 102 can further include a processor, computer readable storage, buttons, switches, and/or one or more wireless or wired communication units to enable automatic, programmed, remote, or local control of the operations, such as light, drug administration, sensors, data collection and transmission, size or shape or curvature adjustments, or other similar operations.

Figure 2:
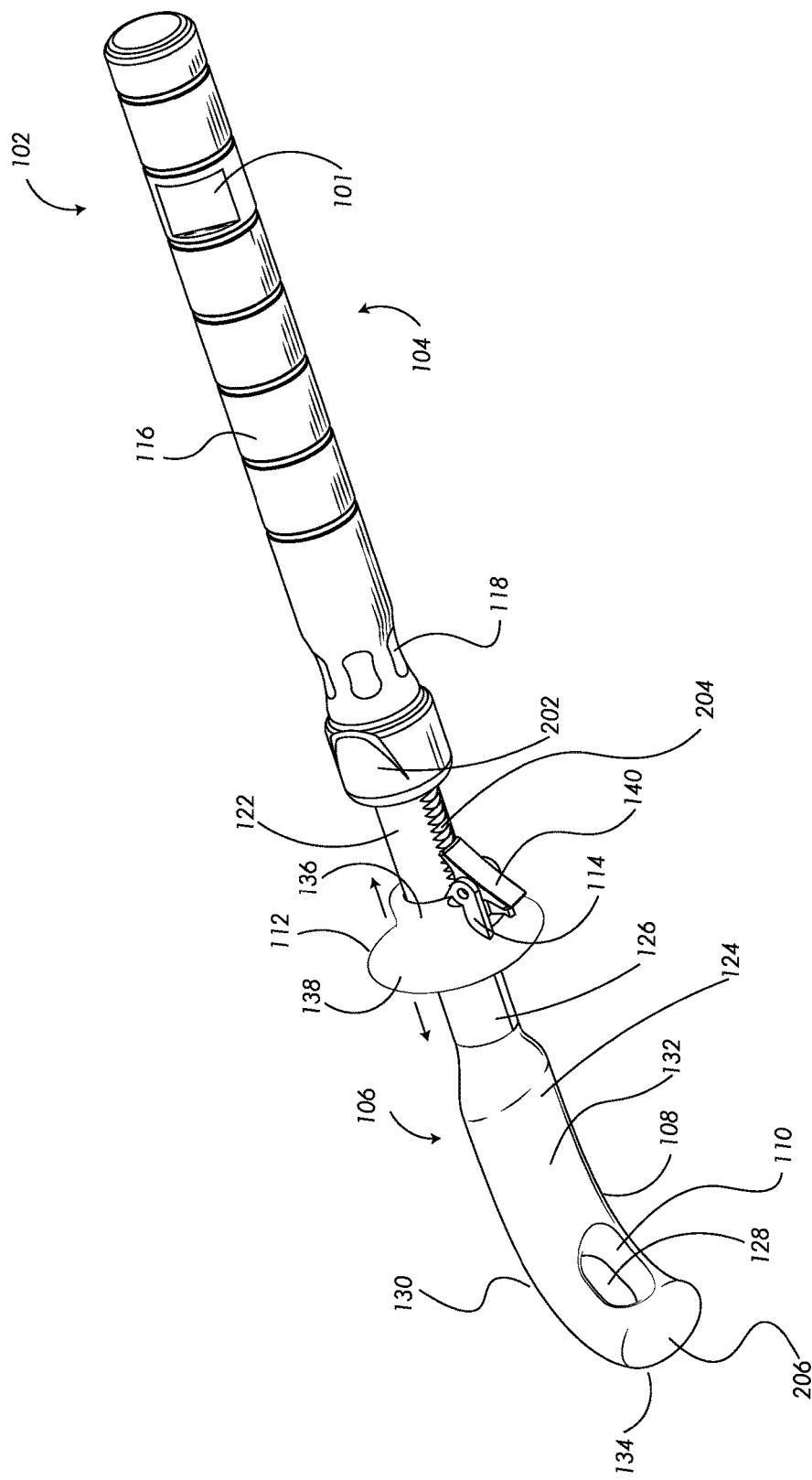
FIG. 2 is a bottom perspective view of a vaginal surgical apparatus, in accordance with an embodiment of the invention.

FIG. 2 is a bottom perspective view of a vaginal surgical apparatus, in accordance with an embodiment of the invention. In one embodiment, an apparatus 102 includes, but is not limited to, an elongated handle portion 104; a vaginal manipulator probe 106 that is at least partly insertable into a vagina, the vaginal manipulator probe 106 extending from the elongated handle portion 104 and including an arcuate end portion 108, the arcuate end portion 108 including an aperture 110 for accommodating a cervix; and a disk 112 that is movable along at least a portion of a length of the vaginal manipulator probe 106, the disk 112 including a locking mechanism 114 to releasably secure the disk 112 in position to limit vaginal insertion depth of the vaginal manipulator probe 106. In one particular embodiment, the elongated handle portion 104 is a cylindrical shaft 116. In another embodiment, the elongated handle portion 104 includes a recessed waist portion 118. In certain embodiments, the vaginal manipulator probe 106 is releasable from the elongated handle portion 104. Alternatively, in some embodiments, the vaginal manipulator probe 106 and the elongated handle portion 104 are a unitary structure. In one embodiment, the elongated handle portion 104 includes a first bollard tab (not visible) and a second bollard tab 202 opposite the first bollard tab for releasably securing a suture. In further embodiments, the vaginal manipulator probe 106 has an oval cross-sectional shape along a length of a longitudinal axis of the vaginal manipulator probe 106. In one particular embodiment, the vaginal manipulator probe 106 includes a first portion 122 having a first cross-sectional width that flares to a second portion 124 having a second cross-sectional width that is greater than the first-cross-sectional width, wherein the first portion 122 and the second portion 124 have substantially similar cross-sectional heights. In some embodiments, the vaginal manipulator probe 106 includes a notch track 204 for interfacing with the locking mechanism 114 of the disk 112. In additional embodiments, the vaginal manipulator probe 106 includes a linear portion 126 that extends from the arcuate end portion 108. In one particular embodiment, the aperture 110 of the arcuate end portion 108 of the vaginal manipulator probe 106 extends as a channel 128 from a top surface 130 of the vaginal manipulator probe 106 through to a bottom surface 132 of the vaginal manipulator probe 106. In one embodiment, the aperture 110 is positioned approximately midway along a length of the arcuate end portion 108 of the vaginal manipulator probe 106. In other embodiments, the vaginal manipulator probe 106 includes an end portion 134 that curls to define a bullous tip 206. In one specific embodiment, the aperture 110 measures approximately 2 cm to 4 cm across and/or in length. In some embodiments, the disk 112 is movable along a portion of a length of the vaginal manipulator probe 106 having a notch track 204. In further embodiments, the disk 112 includes a sleeve portion 136 that circumscribes the vaginal manipulator probe 106. In other embodiments, the disk 112 includes a shoulder 138 that circumscribes the vaginal manipulator probe 106, the shoulder 138 being operable to rest against an outside surface of a vulva when the vaginal manipulator probe 106 is inserted within the vagina. In a further embodiment, the disk 112 includes a spring-loaded latch 140 that is tensionally biased against a notch track 204 of the vaginal manipulator probe 106.

In one embodiment, an apparatus 102 includes, but is not limited to, an elongated handle portion 104 that includes a first bollard tab (not visible) and a second bollard tab 202 for releasably securing a suture; a vaginal manipulator probe 106 extending from the elongated handle portion 104 and including an arcuate end portion 108 having an oval-cross sectional shape and having an aperture channel 110 for accommodating a cervix; and a disk 112 that is movable along at least a portion of a length of the vaginal manipulator probe 106, the disk 112 including a locking mechanism 114 to releasably secure the disk 112 in position to limit vaginal insertion depth of the vaginal manipulator probe 106.

In another embodiment, an apparatus 102 includes, but is not limited to, an elongated handle portion 104 that includes a first bollard tab (not visible) and a second bollard tab 202 for releasably securing a suture; a vaginal manipulator probe 106 extending from the elongated handle portion 104 and including an arcuate end portion 108 having an oval-cross sectional shape and having an aperture channel 110 for accommodating a cervix, the arcuate end portion 108 terminating to a bullous tip 206; a disk 112 including a sleeve 136 and shoulder 138, the disk 112 being movable along at least a portion of a length of the vaginal manipulator probe 106; and a spring loaded latch 140 associated with the disk 112 to releasably secure the disk 112 in position along a length of the vaginal manipulator probe 106 to limit vaginal insertion depth.

Figure 3:
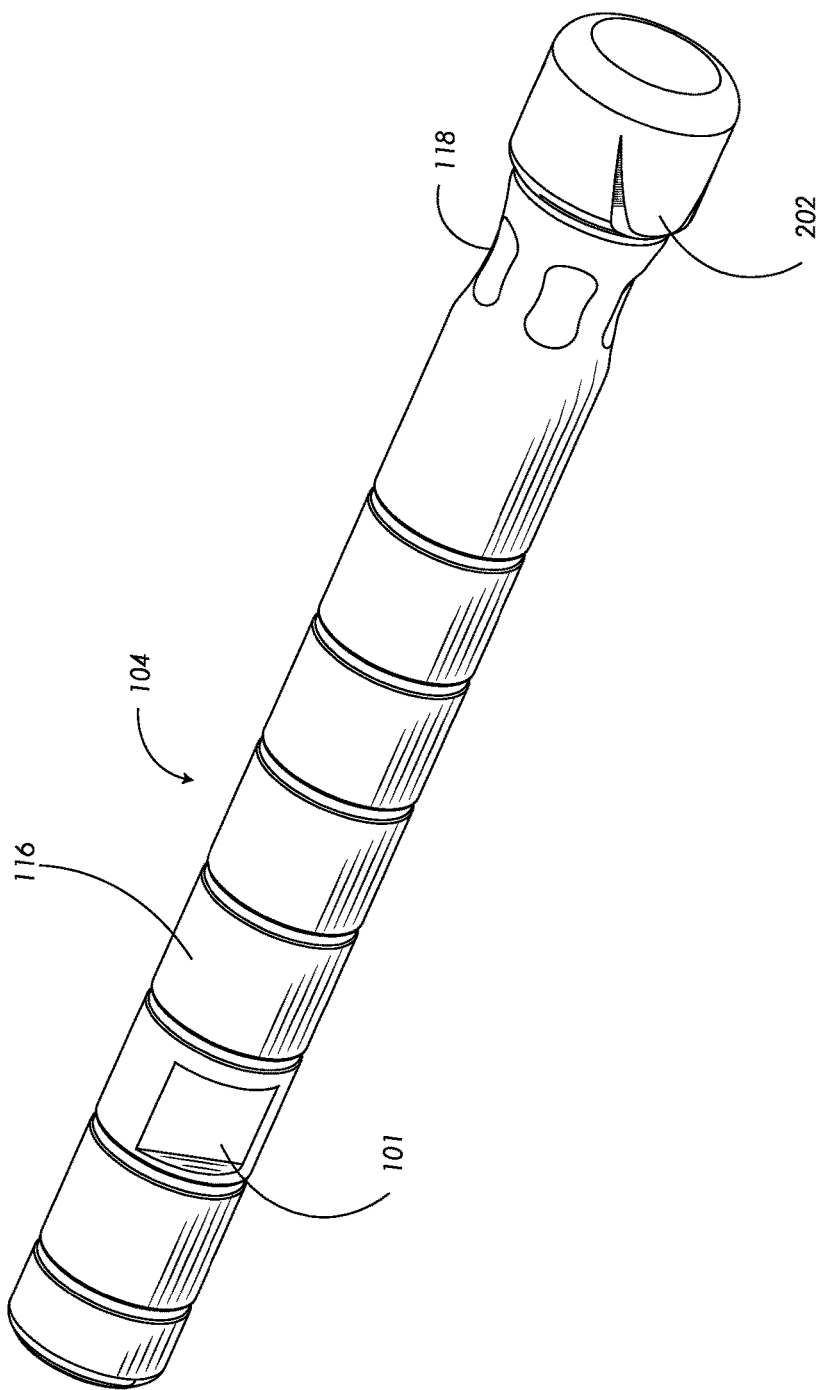
FIG. 3 is a perspective view of a handle portion of a vaginal surgical apparatus, in accordance with an embodiment of the invention.

FIG. 3 is a perspective view of a handle portion of a vaginal surgical apparatus, in accordance with an embodiment of the invention. In one embodiment, the elongated handle portion 104 is a cylindrical shaft 116. In another embodiment, the elongated handle portion 104 includes a recessed waist portion 118. In certain embodiments, the elongated handle portion 104 is releasable from the vaginal manipulator probe (not shown). Alternatively, in some embodiments, the vaginal manipulator probe (not shown) and the elongated handle portion 104 are a unitary structure. In one embodiment, the elongated handle portion 104 includes a first bollard tab (not visible) and a second bollard tab 202 opposite the first bollard tab for releasably securing a suture. In another embodiment, the elongated handle portion 104 includes a notch 101 on opposing sides to define a planar surface for accommodating a clasp, clamp, or other securing mechanism to hold the apparatus in position.

Figure 4:
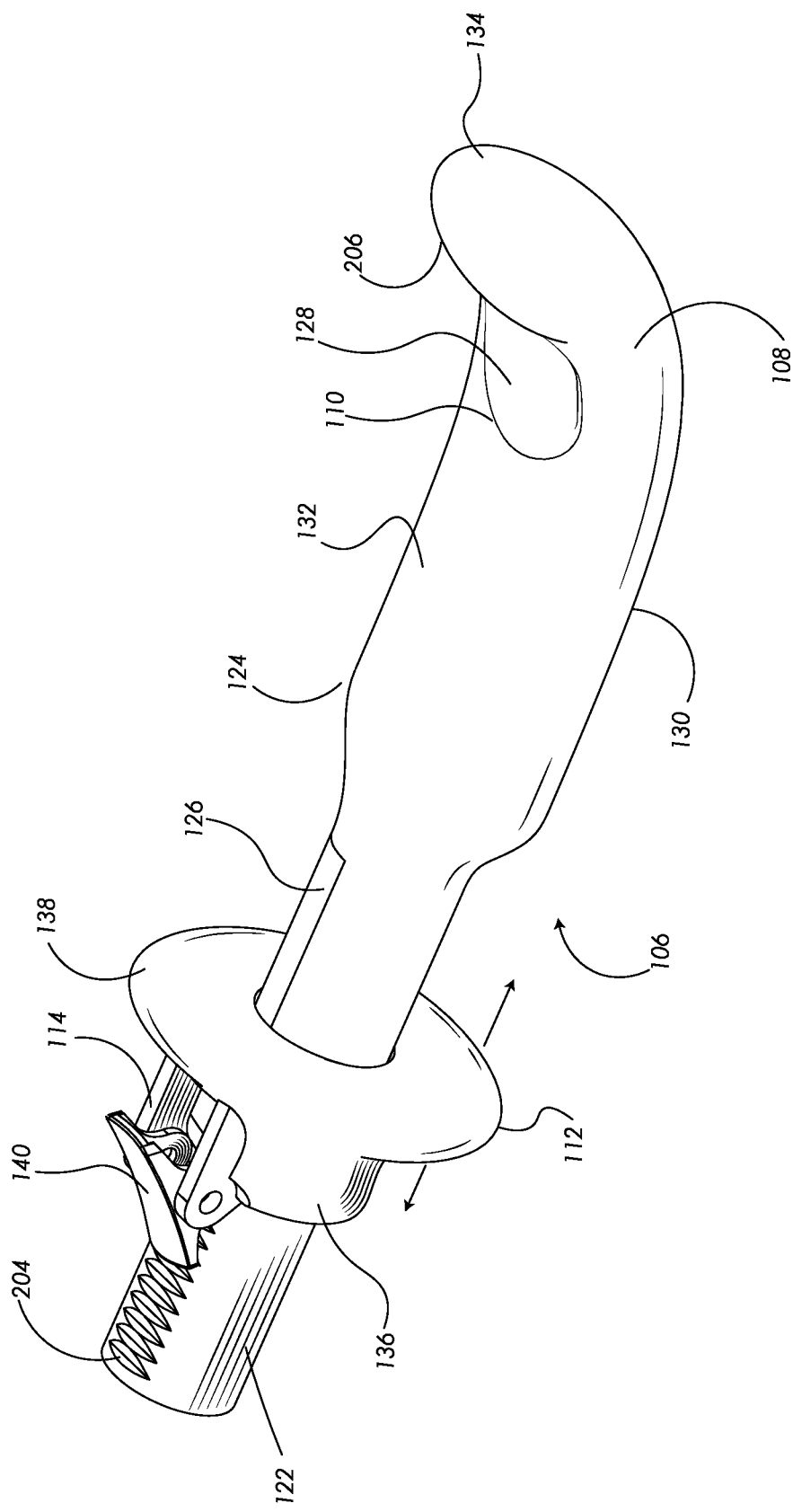
FIG. 4 is a perspective view of a vaginal manipulator probe of a vaginal surgical apparatus, in accordance with an embodiment of the invention.

FIG. 4 is a perspective view of a vaginal manipulator probe of a vaginal surgical apparatus, in accordance with an embodiment of the invention. In one embodiment, the vaginal manipulator probe 106 has an oval cross-sectional shape along a length of a longitudinal axis of the vaginal manipulator probe 106. In one particular embodiment, the vaginal manipulator probe 106 includes a first portion 122 having a first cross-sectional width that flares to a second portion 124 having a second cross-sectional width that is greater than the first-cross-sectional width, wherein the first portion 122 and the second portion 124 have substantially similar cross-sectional heights. In some embodiments, the vaginal manipulator probe 106 includes a notch track 204 for interfacing with the locking mechanism 114 of the disk 112. In additional embodiments, the vaginal manipulator probe 106 includes a linear portion 126 that extends from the arcuate end portion 108. In one particular embodiment, the aperture 110 of the arcuate end portion 108 of the vaginal manipulator probe 106 extends as a channel 128 from a top surface 130 of the vaginal manipulator probe 106 through to a bottom surface 132 of the vaginal manipulator probe 106. In one embodiment, the aperture 110 is positioned approximately midway along a length of the arcuate end portion 108 of the vaginal manipulator probe 106. In other embodiments, the vaginal manipulator probe 106 includes an end portion 134 that curls to define a bullous tip 206. In one specific embodiment, the aperture 110 measures approximately 2 cm to 4 cm across and/or in length. In some embodiments, the disk 112 is movable along a portion of a length of the vaginal manipulator probe 106 having a notch track 204. In further embodiments, the disk 112 includes a sleeve portion 136 that circumscribes the vaginal manipulator probe 106. In other embodiments, the disk 112 includes a shoulder 138 that circumscribes the vaginal manipulator probe 106, the shoulder 138 being operable to rest against an outside surface of a vulva when the vaginal manipulator probe 106 is inserted within the vagina. In a further embodiment, the disk 112 includes a spring-loaded latch 140 that is tensionally biased against a notch track 204 of the vaginal manipulator probe 106.

Figure 5:
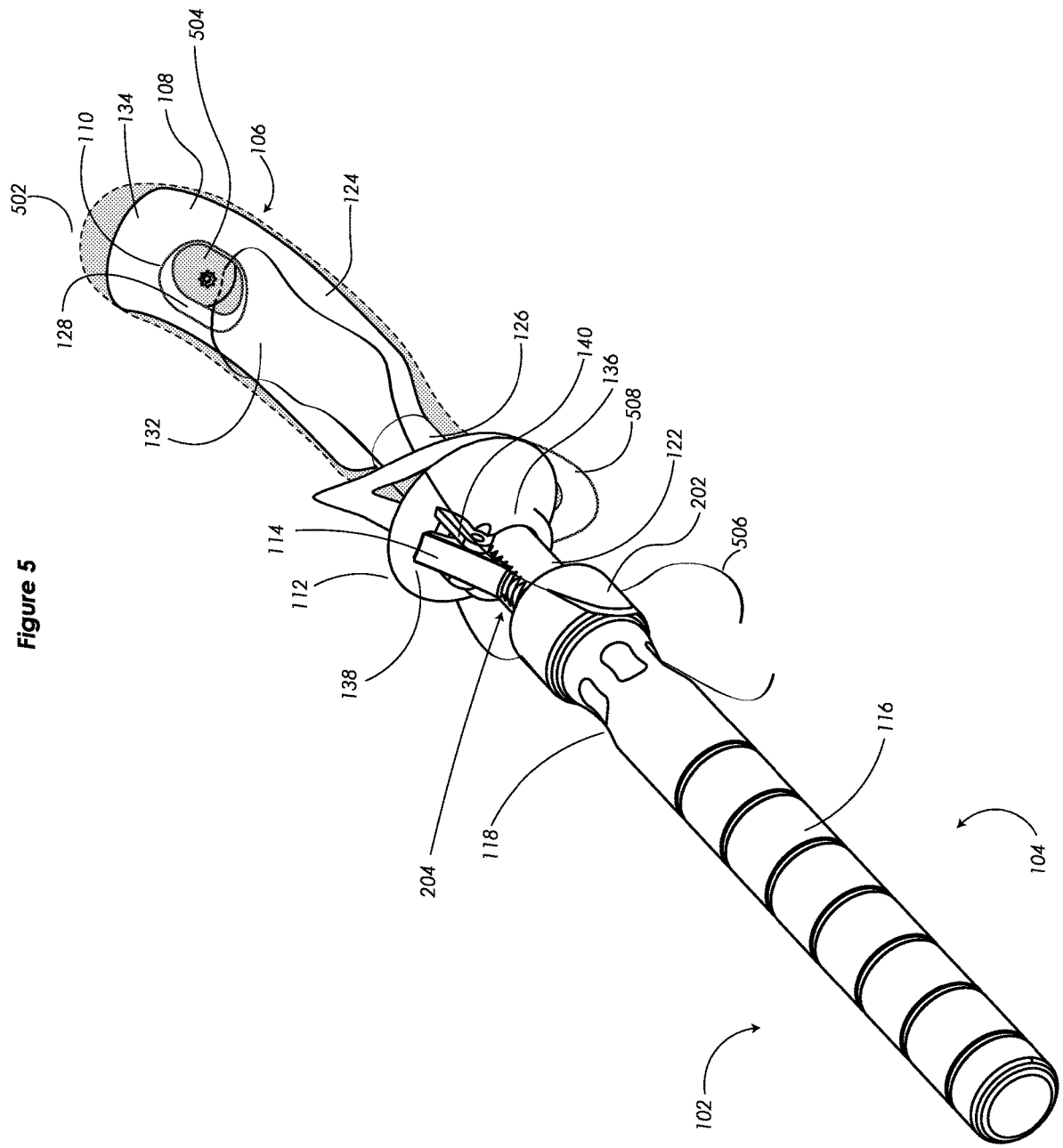
FIG. 5 is a perspective view of a vaginal manipulator probe of a vaginal surgical apparatus inserted into a vaginal space, in accordance with an embodiment of the invention.

FIG. 5 is a perspective view of a vaginal manipulator probe of a vaginal surgical apparatus inserted into a vaginal space, in accordance with an embodiment of the invention. In one embodiment, an apparatus 102 includes, but is not limited to, an elongated handle portion 104; a vaginal manipulator probe 106 that is at least partly insertable into a vagina 502, the vaginal manipulator probe 106 extending from the elongated handle portion 104 and including an arcuate end portion 108, the arcuate end portion 108 including an aperture 110 for accommodating a cervix 504; and a disk 112 that is movable along at least a portion of a length of the vaginal manipulator probe 106, the disk 112 including a locking mechanism 114 to releasably secure the disk 112 in position to limit vaginal insertion depth of the vaginal manipulator probe 106. In one particular embodiment, the elongated handle portion 104 is a cylindrical shaft 116. In another embodiment, the elongated handle portion 104 includes a recessed waist portion 118. In certain embodiments, the vaginal manipulator probe 106 is releasable from the elongated handle portion 104. Alternatively, in some embodiments, the vaginal manipulator probe 106 and the elongated handle portion 104 are a unitary structure. In one embodiment, the elongated handle portion 104 includes a first bollard tab (not visible) and a second bollard tab 202 opposite the first bollard tab for releasably securing a suture 506. In further embodiments, the vaginal manipulator probe 106 has an oval cross-sectional shape along a length of a longitudinal axis of the vaginal manipulator probe 106. In one particular embodiment, the vaginal manipulator probe 106 includes a first portion 122 having a first cross-sectional width that flares to a second portion 124 having a second cross-sectional width that is greater than the first-cross-sectional width, wherein the first portion 122 and the second portion 124 have substantially similar cross-sectional heights. In some embodiments, the vaginal manipulator probe 106 includes a notch track 204 for interfacing with the locking mechanism 114 of the disk 112. In additional embodiments, the vaginal manipulator probe 106 includes a linear portion 126 that extends from the arcuate end portion 108. In one particular embodiment, the aperture 110 of the arcuate end portion 108 of the vaginal manipulator probe 106 extends as a channel 128 from a top surface (not visible) of the vaginal manipulator probe 106 through to a bottom surface 132 of the vaginal manipulator probe 106. In one embodiment, the aperture 110 is positioned approximately midway along a length of the arcuate end portion 108 of the vaginal manipulator probe 106. In other embodiments, the vaginal manipulator probe 106 includes an end portion 134 that curls to define a bullous tip. In one specific embodiment, the aperture 110 measures approximately 2 cm to 4 cm across and/or in length. In some embodiments, the disk 112 is movable along a portion of a length of the vaginal manipulator probe 106 having the notch track 204. In further embodiments, the disk 112 includes a sleeve portion 136 that circumscribes the vaginal manipulator probe 106. In other embodiments, the disk 112 includes a shoulder 138 that circumscribes the vaginal manipulator probe 106, the shoulder 138 being operable to rest against an outside surface of a vulva 508 when the vaginal manipulator probe 106 is inserted within the vagina 502. In a further embodiment, the disk 112 includes a spring loaded latch 140 that is tensionally biased against the notch track 204 of the vaginal manipulator probe 106.

In one embodiment, an apparatus 102 includes, but is not limited to, an elongated handle portion 104 that includes a first bollard tab (not visible) and a second bollard tab 202 for releasably securing a suture 506; a vaginal manipulator probe 106 extending from the elongated handle portion 104 and including an arcuate end portion 108 having an oval-cross sectional shape and having an aperture channel 110 for accommodating a cervix 504; and a disk 112 that is movable along at least a portion of a length of the vaginal manipulator probe 106, the disk 112 including a locking mechanism 114 to releasably secure the disk 112 in position to limit vaginal insertion depth of the vaginal manipulator probe 106.

In another embodiment, an apparatus 102 includes, but is not limited to, an elongated handle portion 104 that includes a first bollard tab (not visible) and a second bollard tab 202 for releasably securing a suture 506; a vaginal manipulator probe 106 extending from the elongated handle portion 104 and including an arcuate end portion 108 having an oval-cross sectional shape and having an aperture channel 110 for accommodating a cervix 504, the arcuate end portion 108 terminating to a bullous tip; a disk 112 including a sleeve 136 and shoulder 138, the disk 112 being movable along at least a portion of a length of the vaginal manipulator probe 106; and a spring loaded latch 140 associated with the disk 112 to releasably secure the disk 112 in position along a length of the vaginal manipulator probe 106 to limit vaginal insertion depth.

Figure 6:
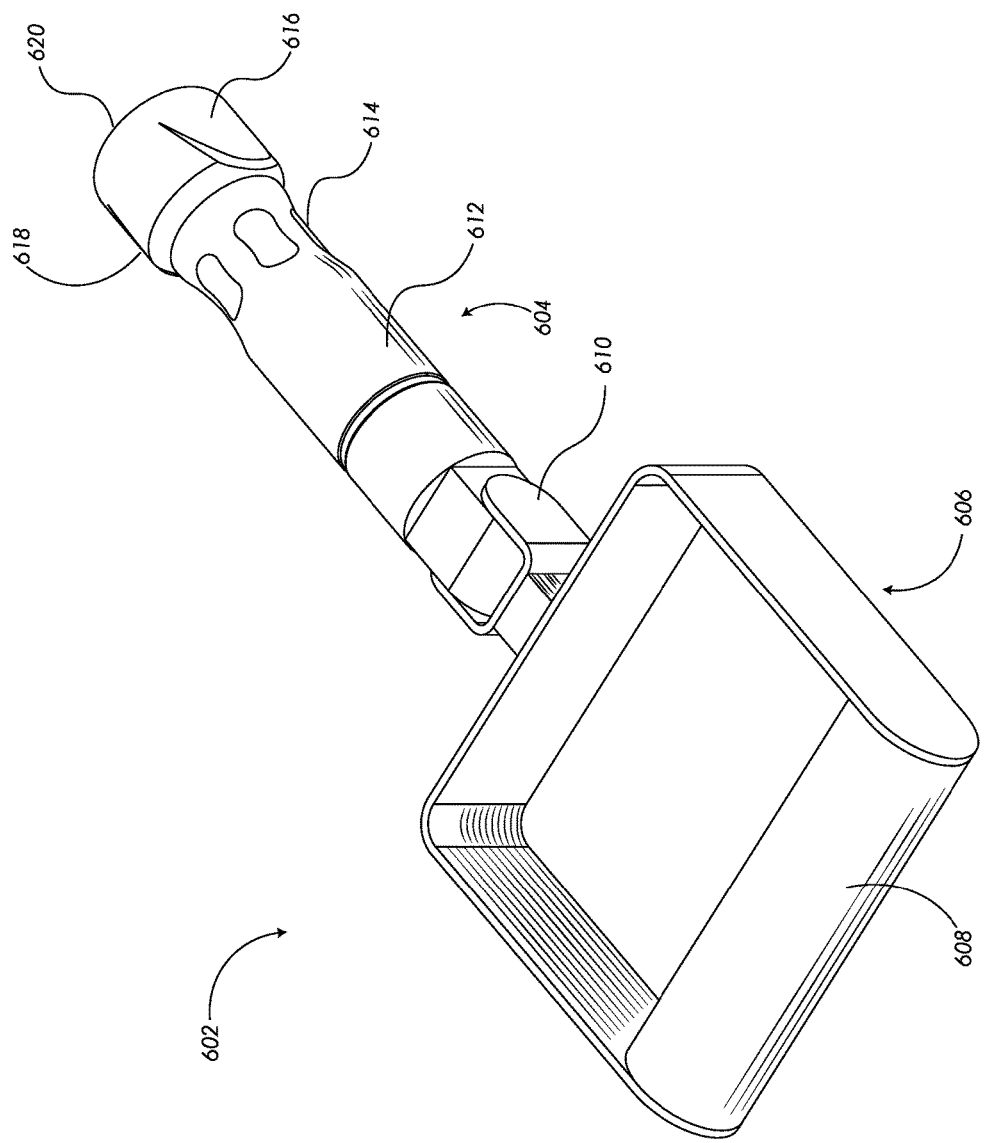
FIG. 6 is a perspective view of a movable handle of a vaginal surgical apparatus, in accordance with an embodiment of the invention.

FIG. 6 is a perspective view of a movable handle of a vaginal surgical apparatus, in accordance with an embodiment of the invention. In one embodiment, a movable handle 602 includes an elongated portion 604 movably coupled to a handle portion 606 via an articulating joint 610. The handle portion 606 includes a grip. The elongated portion 604 includes a shaft with a recessed waist 614 terminating at a vaginal manipulator probe attachment end 620. The shaft 612 can include a first bollard tab 616 and a second bollard tab 618 for securing one or more sutures (not visible). Accordingly, the movable handle 602 can be used in conjunction with various embodiments disclosed herein to provide an alternative handle structure for manipulating a vaginal manipulator probe 106.

In certain embodiments, wherein the elongated portion 604 is a cylindrical shaft. In other embodiments, the elongated portion 604 includes a recessed waist 614 for accommodating a thumb. In other embodiments, the elongated portion 604 is releasable from a vaginal manipulator probe 106. In further embodiments, the elongated portion 604 and a vaginal manipulator probe are provided as a unitary structure.

In some embodiments, the handle portion 606 rotates and/or pivots relative to the elongated portion 604. The articulating joint 610 can permit movement in one, two, or three directions, such as being capable of adjustably extending from the elongated portion 604. In certain embodiments, the articulating joint is lockable in one or more positions via friction, a locking mechanism (e.g., pin, screw, jam nut, or similar structure), or is freely movable. In other embodiments, the handle portion 606 includes a shaft grip, a knob, one or more finger holes, or a differently configured grip 608 (e.g., narrower, wider, thicker, thinner, etc.).

In further embodiments, the shaft 612 is differently configured, such as shorter, longer, wider, non-linear, squared, or the like. The shaft 612 can be removably coupled to the vaginal manipulator probe as discussed herein, or can be part of a unitary structure with the vaginal manipulator probe. The recessed waist 614 can be differently positioned, duplicated, longer, deeper, shorter, or even omitted. The first and second bollard tabs 616 and 618 can be omitted or differently positioned, such as on a rotatable or movable sleeve.

In one particular embodiment, a movable handle 602 is similar to the part that you hold on a child's red wagon. The movable handle 602 can be an option to slip onto or couple with the vaginal manipulator probe 106. The movable handle 602 can be secured in place with a spring-loaded button or other simple device, and have a short extension which swivels in the anterior-posterior plane only allowing several handle positions, perhaps three. The movable handle 602 includes an opening (where the surgeon's fingers would be located) which enables access to the anal canal with a separate probe.

In one other particular embodiment, the elongated portion 104 or 604 has a bend or is offset from a midline to define a space that accommodates a rectal probe (which extending straight out of the anus) without conflicting with each other. This allows for easier positioning of the apparatus. It would also allow easier positioning of the apparatus 102 while concurrently suing a rectal probe—maintaining the apparatus 102 in the midline, rather than having it at an eccentric angle.

Figure 7:
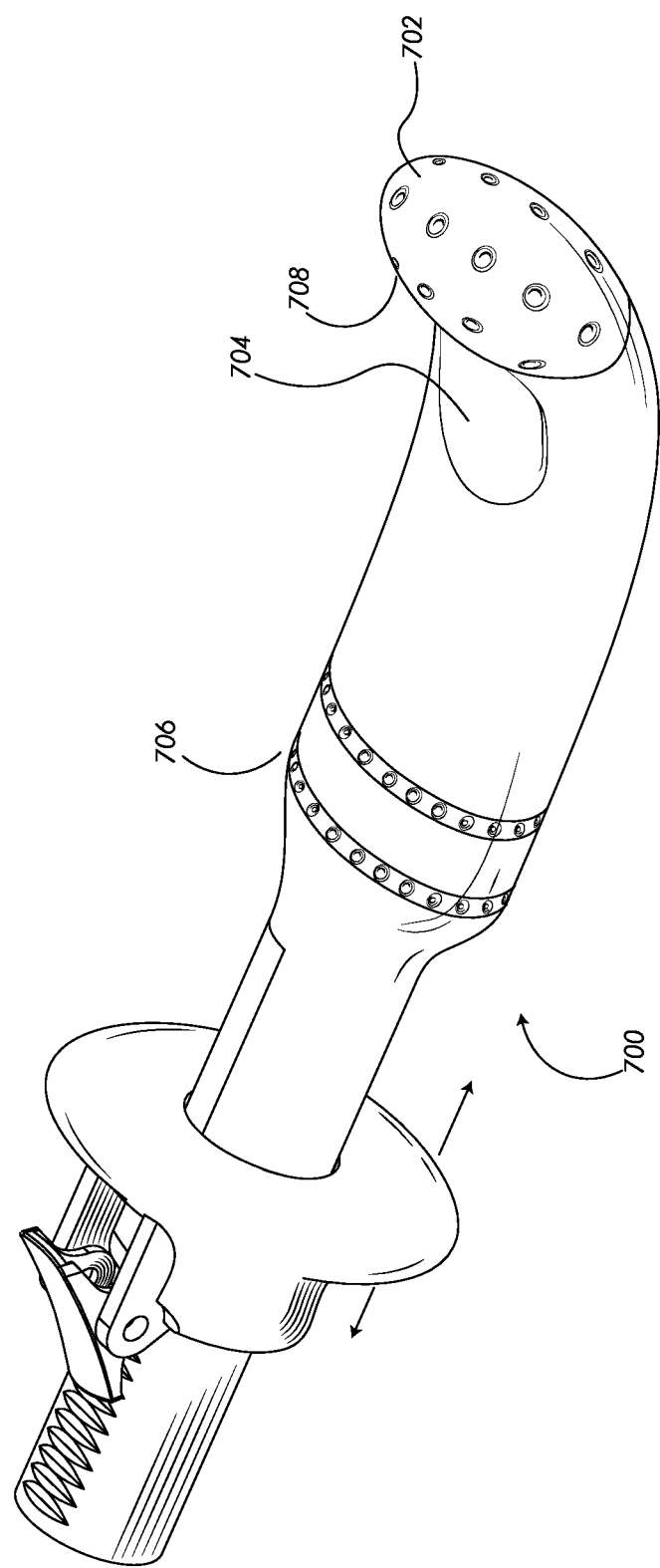
FIG. 7 is a perspective view of a vaginal surgical apparatus with one or more prominence features, in accordance with an embodiment of the invention.

FIG. 7 is a perspective view of a vaginal surgical apparatus with one or more prominence features, in accordance with an embodiment of the invention. In one instance, an apparatus includes, but is not limited to, a vaginal manipulator probe 700 that is at least partly insertable into a vagina, the vaginal manipulator probe including an end portion 702 that includes a bullous tip and that includes a space 704 that accommodates a cervix therewithin; and at least one prominence 706 incorporated with the vaginal manipulator probe 700 operable to assist with identifying one or more positions of at least one anatomical structure or orienting the vaginal manipulator probe 700. In one particular embodiment, the prominence 706 comprises at least one light prominence incorporated with the vaginal manipulator probe 700 operable to assist with identifying one or more positions of at least one anatomical structure or orienting the vaginal manipulator probe. For example, the prominence 706 can includes at least one light line incorporated with the vaginal manipulator probe 700 operable to assist with identifying one or more positions of at least one anatomical structure or orienting the vaginal manipulator probe 700. Alternatively or additionally, the probe 700 can include at least one light surface 708 incorporated with the vaginal manipulator probe operable to assist with identifying one or more positions of at least one anatomical structure or orienting the vaginal manipulator probe 700. In certain embodiments, the at least one light prominence 706 or light surface 708 is incorporated around a circumference of the vaginal manipulator probe 700 operable to assist with identifying one or more positions of at least one anatomical structure or orienting the vaginal manipulator probe 700. Further, the at least one light prominence 706 or light surface 708 can be incorporated on a surface of the vaginal manipulator probe 700 operable to assist with identifying one or more positions of at least one anatomical structure or orienting the vaginal manipulator probe 700. In one specific embodiment, the at least one light prominence 706 or light surface 708 can be incorporated at a tip of the vaginal manipulator probe 700 operable to assist with identifying one or more positions of at least one anatomical structure or orienting the vaginal manipulator probe 700. In another particular embodiment, the probe 700 can include at least one two light prominences 706 or light surfaces 708 of different colors incorporated with the vaginal manipulator probe 700 operable to assist with identifying one or more positions of at least one anatomical structure or orienting the vaginal manipulator probe 700. The at least one prominence 706 or 708 can be incorporated with the vaginal manipulator probe 700 operable to assist with identifying an insertion distance of the vaginal manipulator probe 700 relative to an anatomical structure. Additionally or alternatively, the at least one prominence 706 or 708 can be incorporated with the vaginal manipulator probe 700 operable to assist with positioning the vaginal manipulator probe 700 relative to an anatomical structure.

This technology disclosure can assist a surgeon in identifying anatomic landmarks which would facilitate accuracy of graft placement and the timely completion of sacrocolpopexy-type procedures. There are issues solved related to identifying the extent of dissection between the vagina and the rectum posteriorly and the bladder anteriorly. On the posterior recto-vaginal interface, the dissection is ideally extended down from above to the pelvic floor, where the graft may then be sutured into position. It can be difficult to identify when this depth is reached. Having a prominence such as a bright LED in the probe enables visual perception through the tissues about, for example, 1 cm above the perineal disc, and perhaps others at, for example, 2 and 3 cm above, to allow for atomic variation and help a surgeon know the dissection was complete. This can be done without necessitating an external exam to verify, saving time and expense.

Similarly on the anterior interface between vagina and bladder, a series of prominence features, such as lights could identify where the bladder trigone is beginning and therefore the dissection complete. For example, LEDs could be around 5-8 cm above the perineal disc on the top surface of the probe.

Other options which improve the ability of a surgeon to identify anatomic areas and/or maintain the vagina and cervix in the proper position during vaginal and/or rectal prolapse procedures include, but are not limited to: a series of circumferential lights, for example as a thin band encircling the probe shaft to mark a certain distance and that are bright enough to be seen through the tissue by the surgeon operating laparoscopically (e.g., 1 or 2 cm from the hymen or probe perineal disc and then another band at 5 cm and then finally a lighted broader area at the probe tip to indicate the position of the vaginal apex).

The lights can be manufactured with simple, inexpensive materials, and/or could be disposable. The lights can be either connected to a light source in the operating room via optical fibers, or can be independent LED lights with small batteries. Lighted features or bands can vary in width and location long the probe shaft and/or can use different colors to indicate different depths, such as white, red, and blue. The tip light could be a different configuration such as solid or a continuous series along the tip.

Additionally or alternatively, the probe shaft could be hollow with a single or multiple internal bright lights within it and the "lighted band" or prominence could simply be a clear plastic ring allowing the transmission of light from that internal source. The internal probe light could provide light for both bands and the tip, eliminating the need for multiple lights and complexity. Another simpler design could be a single circular light (or clear plastic light-transmissible material), created by an LED or other internal probe source, with the result looking like the end of a flashlight. This could be perhaps 2-10 mm diameter with a single posterior position about 2 cm above the average position of the perineal disc, and in an anterior position about 7 cm above the perineal disc, corresponding to the level of the internal pelvic floor muscles (posteriorly) and the top of the bladder trigone (anteriorly), respectively.

Figure 8:
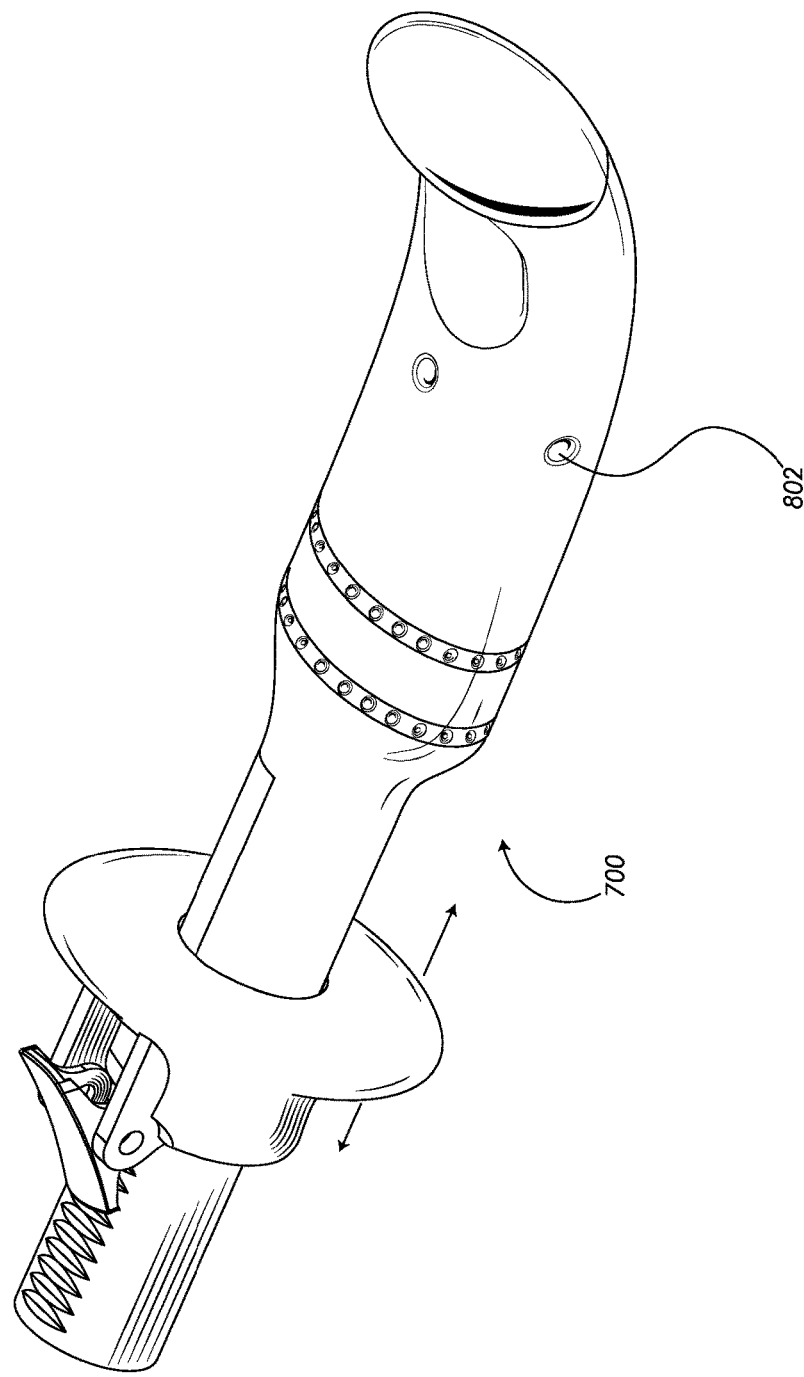
FIG. 8 is a perspective view of a vaginal surgical apparatus with one or more prominence features, in accordance with an embodiment of the invention.

FIG. 8 is a perspective view of a vaginal surgical apparatus with one or more prominence features, in accordance with an embodiment of the invention. In one embodiment, the probe 700 can include one or more prominences 802 positioned at various points about a surface of the probe to assist with orienting the probe 700 relative to tissue. For instance, there can include spaced single lights with one on each side and one in middle, just one in middle, just on a side, etc. to assist with orientation of the probe 700 or tip in the midline of the vaginal cuff. Also, as an additional light-option, a single posterior lighted area closer to the disc and a higher single lighted area anteriorly can be employed. There may also include a topographically-adjustable "prominence" which may or not include a lighted feature.

Note that any of the features and embodiments disclosed and illustrated with respect to FIGS. 7 and 8 may further include any of the features or embodiments disclosed and illustrated elsewhere in the specification and drawings. Likewise, other portions of the specification and drawings can incorporate any of the features and embodiments disclosed and illustrated with respect to FIGS. 7 and 8.

Figure 9:
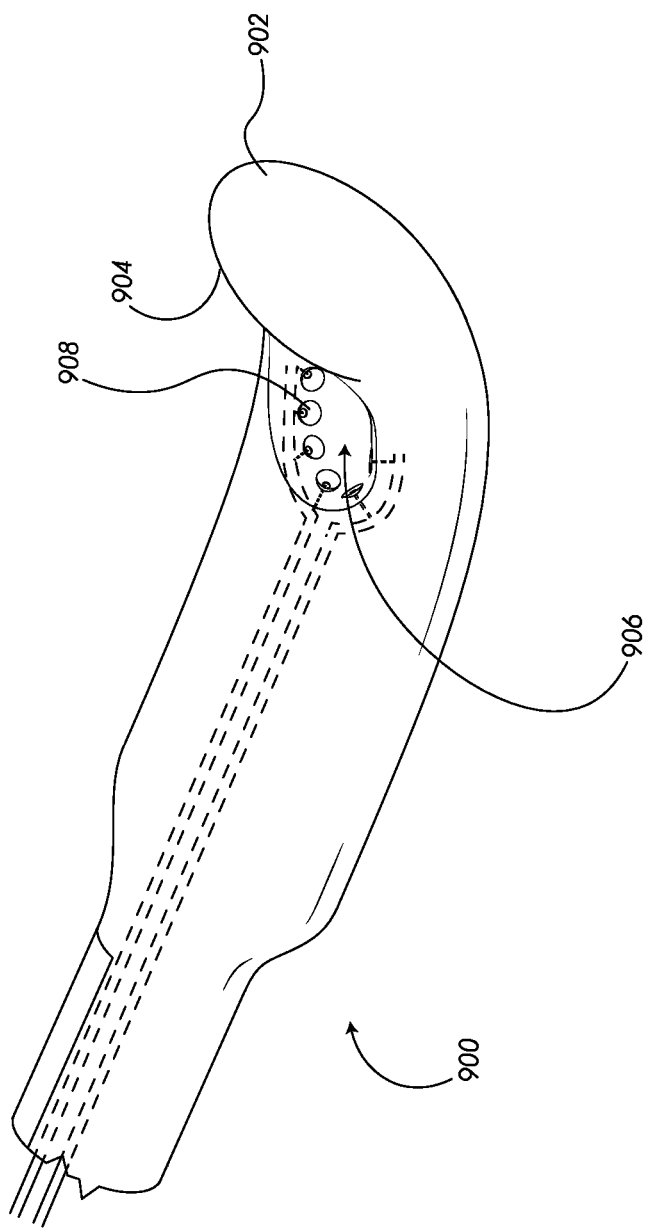
FIG. 9 is a perspective view of a vaginal surgical apparatus with one or more suction ports, in accordance with an embodiment of the invention.

FIG. 9 is a perspective view of a vaginal surgical apparatus with one or more suction ports, in accordance with an embodiment of the invention. In one embodiment, an apparatus includes, but is not limited to, a vaginal manipulator probe 900 that is at least partly insertable into a vagina, the vaginal manipulator probe 900 including an end portion 902 that includes a bullous tip 904 and that includes a space 906 that accommodates a cervix therewithin; and at least one suction mechanism 908 incorporated with the vaginal manipulator probe 900 operable to assist with stabilizing the vaginal manipulator probe 900 relative to tissue. In one embodiment, the at least one suction mechanism 908 comprises at least one suction cup incorporated within a cervical well or on a surface of the vaginal manipulator probe operable to assist with stabilizing the vaginal manipulator probe relative to tissue.

The tissue stabilization device disclosed herein can be applied to a gynecologic surgery. The probe can be inserted into the vagina, positioned with the cervix in the well, and suction can be applied (e.g., using a valve control) to maintain probe for the surgery. To reposition, the suction is released and the device is repositioned before suction is applied again.

Many alternative embodiments are possible. For example, the cupped portion which accepts a cervix can have suction holes embedded in it which are connected to wall suction at the opposite probe end which is outside the body. A valve can be included to apply the suction when the device is placed (e.g., close the valve to maintain the suction or re-open the valve if repositioning is needed). These suction holes or cups, similar to a starfish or octopus, could also be available over different sections of the probe tip and shaft if needed to maintain the orientation of the vaginal mucosa adjacent to the probe and prevent the probe "wandering" to an incorrect position which often occurs during a procedure. A series valves can be associated with a manifold that provides reduced pressure (suction) to different portions of the probe or to any combination of the valves. The suction can be powerful enough to hold the probe in place without connection to an outside-the-body device.

In additional embodiments, the suction can be provided via one or several suctions cups of differing sizes, such as several 3-4 mm cups or one 2 cm central cup. The suction cups can be rounded, linear, or any other shape. Small, funnel-shaped silicone suction cups could be pressed into holes positioned around the inside of walls of the cervical well. These soft silicone suction cups can be removed easily if not desired. The suction cups can connect to plastic tubing within the probe, which then connects to a manifold to accommodate up to 4 separate tubes, then to a three-way stop-cock valve, to which the operating room suction tubing could be connected to apply suction. Alternatively, there can be a single connection tube from the cervical well suction to a valve. The device can optionally include silicone plugs or tape to occlude the holes or a portion of the holes to allow for use of one size cervical well to work with different cervical sizes. For example, the surgeon might elect to have the tissue stabilization suction limited to part of the well to hold a smaller cervix, which would allow the suction to contact a portion of the cervix. Alternatively, there can be multiple (e.g., 3-4) suction cups in the deepest part of the cervical well which could hold the tissue for a wide variety of cervical sizes without attempting to fit the cervix width exactly.

In certain embodiments, the suction can be provided by multiple small cups around the periphery, multiple (e.g., 3-4) larger central cups in the area of the depression for the cervix, a single large cup in the area, a shallow depression for the cervix with a single central cup extending beyond the edge of the probe surface which can contact the vaginal mucosa (e.g, for patients who no longer have a cervix (already had a hysterectomy)), and/or a single cup centrally located on the tip in the middle at the end of the probe, such as between or intermixed with lights (e.g, there can be a light on each side and the suction cup in the middle).

One particular design can include a removable suction cup with a threaded "neck" which can be moved from the cervical depression area to the tip area in cases where the cervix was missing or in a different position. Thus, the cup can be easily moved to the tip and threaded into position, while the other hole can be sealed with a threaded plug or push-in silicone plug to maintain the vacuum.

Figure 10:
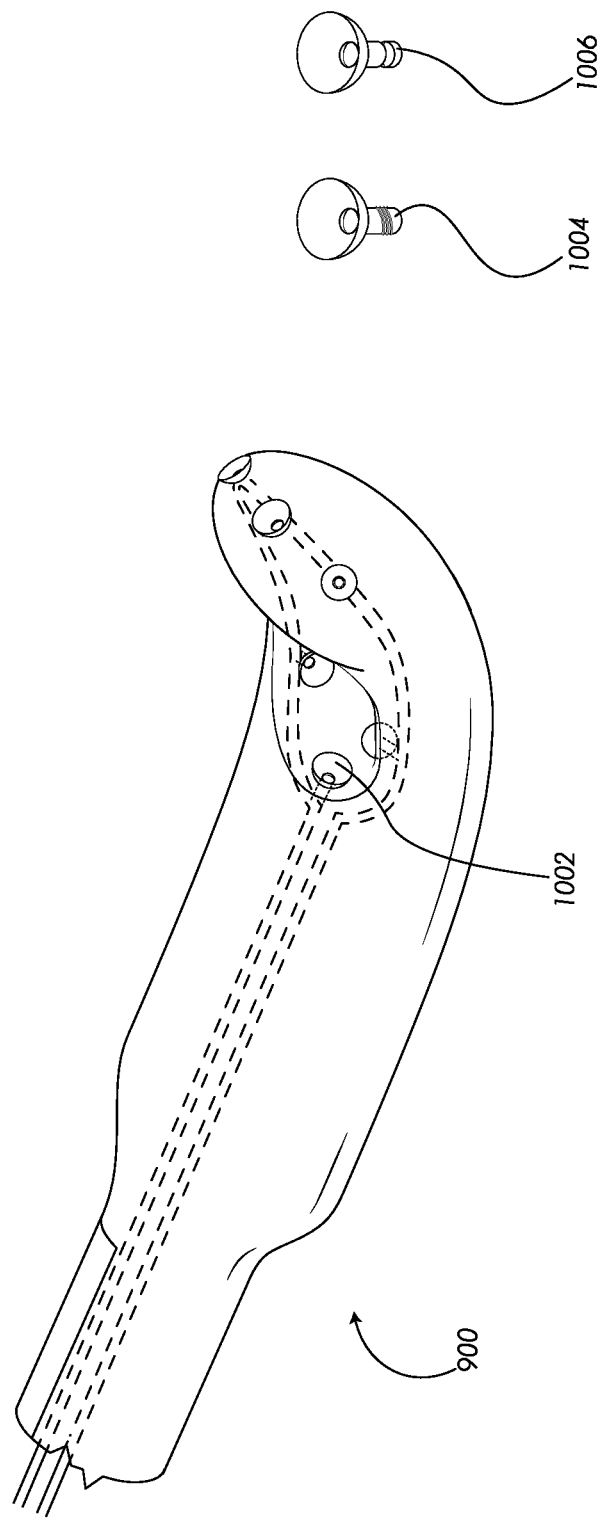
FIG. 10 is a perspective view of a vaginal surgical apparatus with one or more suction ports and removable suction cups, in accordance with an embodiment of the invention.

FIG. 10 is a perspective view of a vaginal surgical apparatus with one or more suction ports and removable suction cups, in accordance with an embodiment of the invention. In one embodiment, an apparatus includes, but is not limited to, a plurality of differential suction mechanisms 1002 incorporated with the vaginal manipulator probe 900 operable to assist with stabilizing the vaginal manipulator probe 900 relative to tissue.

In certain embodiments, the suction mechanism 1002 can include one or more various types of suction cups, including threaded suction cups 1004 and snap-in suction cups 1006. The threaded suction cups 1004 can include screw type threads that spin into one or more orifices in the probe 900. The snap-in suction cups 1006 can be friction fit or mechanically fit (e.g. protrusion or ring prominence engaged into mating portion) into one or more orifices in the probe 900. A plurality of orifices can be positioned over sides, top, bottom, tip, cervical well to receive the suction cups 1004 and/or 1006. Unused orifices can be plugged using thread or snap in type plugs to maintain the suction pressure. The cups 1004 and/or 1006 can include different cup shapes and/or sizes (e.g., square, rectangular, irregular, circular, oval, triangular and/or small, medium, large, extra-large sizes). The cups themselves can include light or permit light to pass (e.g., translucent) similar to the other prominences disclosed herein for positioning and depth insertion determinations.

Note that any of the features and embodiments disclosed and illustrated with respect to FIGS. 9 and 10 may further include any of the features or embodiments disclosed and illustrated elsewhere in the specification and drawings. Likewise, other portions of the specification and drawings can incorporate any of the features and embodiments disclosed and illustrated with respect to FIGS. 9 and 10.

FIG. 11 is a perspective view of a vaginal surgical apparatus with one or more movable prominence features, in accordance with an embodiment of the invention. In one embodiment, at least one light prominence 1102 is incorporated with the vaginal manipulator probe 1100 operable to assist with identifying one or more positions of at least one anatomical structure or orienting the vaginal manipulator probe 1100. For example, the light prominence 1102 can include at least one light ring that is incorporated with the vaginal manipulator probe 1100 operable to assist with identifying one or more positions of at least one anatomical structure or orienting the vaginal manipulator probe 1100. The light prominence 1102 can include at least one movable or repositionable light prominence 1102 that is incorporated with the vaginal manipulator probe 1100 operable to assist with identifying one or more positions of at least one anatomical structure or orienting the vaginal manipulator probe 1100. Alternatively, the light prominence 1104 can be incorporated along a portion of a length of the vaginal manipulator probe 1100 operable to assist with identifying one or more positions of at least one anatomical structure or orienting the vaginal manipulator probe 1100.

With regard to the lighted bands on the probe shaft, their location would vary depending on the depth of the vagina, and therefore would indicate the distance the probe has been inserted up to the adjustable perineal disc. This distance could be set by a surgeon at the time of application and can be adjustable (e.g., would be within a predictable range, such as 1-8 cm from the perineal disc). The lighted band or bands can surround the probe shaft and move similar to sliding a washer up or down a bolt or can move by rolling. Additionally, the added prominence of the lighted band above the surface of the probe would create another useful feature, namely that the surgeon can palpate the "bump" on the other side (the abdominal side) of the tissue. Thus, even without a light, because in some cases the band is unlit, the prominence itself creates a landmark to indicate the corresponding anatomic feature (e.g., the inner surface of the pelvic floor muscles) which is the appropriate depth to stop the dissection from above. A similar feature is provided with an additional lighted band higher up on the shaft, which can indicate the cephalic border of the bladder trigone. Again, due to its palpability, this prominence would be effective even if there was no visible light. Any of the aforementioned bands can be secured using a series of dimples 1106 along a length that resist movement of the band or can be secured by a cam lever, thumb screw, clip, or other mechanism. In the case of the lit bands, wire leads can be provided or the band can have a metal contact portion that interfaces with metal contact on the probe shaft (e.g., metal contact portions in the dimples 1106 can transfer electrons to the band for light power). Alternatively, the bands can be glowing or translucent and illuminated, such as via a light source positioned at the dimple portions 1106.

In certain embodiments, lights can be along the probe body in the anterior and posterior midline. The difference being the anterior lighted region would be further "inside" the patient than the posterior lighted area. For example, the anterior band would span the distance from the perineum of approximately 5-9 cm, while on the posterior side it would be 1-4 cm.

Note that any of the features and embodiments disclosed and illustrated with respect to FIG. 11 may further include any of the features or embodiments disclosed and illustrated elsewhere in the specification and drawings. Likewise, other portions of the specification and drawings can incorporate any of the features and embodiments disclosed and illustrated with respect to FIG. 11.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. An apparatus comprising:
a vaginal manipulator probe that is at least partly insertable into a vagina, the vaginal manipulator probe including an end portion that includes a tip and that includes a space that is configured to accommodate a cervix at least partly therewithin; and
at least two light prominences of different colors incorporated with the vaginal manipulator probe and operable to assist with positioning or orienting the vaginal manipulator probe.

2. The apparatus of claim 1, wherein at least one of the at least two light prominences comprises at least one light ring.

3. The apparatus of claim 1, wherein at least one of the at least two light prominences comprises at least one light surface.

4. The apparatus of claim 1, wherein at least one of the at least two light prominences comprises at least one light line.

5. The apparatus of claim 1, wherein at least one of the at least two light prominences is incorporated around a circumference of the vaginal manipulator probe.

6. The apparatus of claim 1, wherein at least one of the at least two light prominences is incorporated along a portion of a length of the vaginal manipulator probe.

7. The apparatus of claim 1, wherein at least one of the at least two light prominences is incorporated on a surface of the vaginal manipulator probe.

8. The apparatus of claim 1, wherein at least one of the at least two light prominences is incorporated at the tip of the vaginal manipulator probe.

9. The apparatus of claim 1, wherein at least one of the at least two light prominences is operable to assist with identifying an insertion distance of the vaginal manipulator probe.

10. The apparatus of claim 1, wherein at least one of the at least two light prominences is operable to assist with maintaining an orientation of the vaginal manipulator probe.

11. An apparatus comprising:
a vaginal manipulator probe that is at least partly insertable into a vagina, the vaginal manipulator probe including an end portion that includes a tip and that includes a space configured to accommodate a cervix at least partly therewithin; and at least one suction orifice incorporated with the vaginal manipulator probe and operable to assist with stabilizing the vaginal manipulator probe relative to tissue.

12. The apparatus of claim 11, wherein the at least one suction orifice comprises at least one suction cup.

13. The apparatus of claim 11, wherein the at least one suction orifice comprises a plurality of differently sized suction cups.

14. The apparatus of claim 11, further comprising: at least one adjustable suction valve.

15. The apparatus of claim 11, further comprising: one or more suction plugs.

16. The apparatus of claim 11, wherein the at least one suction orifice is incorporated within a cervical well or on a surface of the vaginal manipulator probe.

17. The apparatus of claim 11, wherein the at least one suction orifice further comprises:
at least one removable suction cup.

18. An apparatus comprising:
a vaginal manipulator probe that is at least partly insertable into a vagina, the vaginal manipulator probe including an end portion that defines a space that is configured to accommodate a cervix at least partly therewithin; and
at least one movable or repositionable light prominence associated with the vaginal manipulator probe and operable to assist with positioning or orienting the vaginal manipulator probe.

19. The apparatus of claim 18, wherein the at least one movable or repositionable light prominence comprises at least one light ring.

20. The apparatus of claim 18, wherein the at least one movable or repositionable light prominence comprises at least one light band.

21. The apparatus of claim 18, wherein the at least one movable or repositionable light prominence further defines a bump-type landmark.

22. The apparatus of claim 18, wherein the at least one movable or repositionable light prominence derives its light by glowing.

* * * * *